United States Patent
Pearson et al.

(10) Patent No.: US 8,968,384 B2
(45) Date of Patent: Mar. 3, 2015

(54) CIRCUMFERENTIALLY CONSTRAINING SUTURES FOR A STENT-GRAFT

(75) Inventors: Meghan Pearson, Santa Rosa, CA (US); Emilie Simmons, Cotati, CA (US); Stephen Pearce, Santa Rosa, CA (US); Stephannie Rundle, Santa Rosa, CA (US); Ana Zavala, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 127 days.

(21) Appl. No.: 13/458,076

(22) Filed: Apr. 27, 2012

(65) Prior Publication Data

US 2013/0289713 A1 Oct. 31, 2013

(51) Int. Cl.
*A61F 2/82* (2013.01)
*A61F 2/07* (2013.01)
*A61F 2/954* (2013.01)
*A61F 2/06* (2013.01)
*A61F 2/95* (2013.01)

(52) U.S. Cl.
CPC . *A61F 2/07* (2013.01); *A61F 2/954* (2013.01); *A61F 2002/067* (2013.01); *A61F 2002/075* (2013.01); *A61F 2002/9511* (2013.01); *A61F 2002/9517* (2013.01)
USPC .................................. 623/1.13

(58) Field of Classification Search
CPC .............. A61F 2/07; A61F 2002/8483; A61F 2002/065; A61F 2/86
USPC .............................. 623/1.35–1.36
See application file for complete search history.

(56) References Cited

U.S. PATENT DOCUMENTS

| | | | |
|---|---|---|---|
| 5,425,765 A | 6/1995 | Tiefenbrun et al. | |
| 5,507,771 A * | 4/1996 | Gianturco | 606/198 |
| 5,617,878 A | 4/1997 | Taheri | |
| 5,779,732 A * | 7/1998 | Amundson | 623/1.15 |
| 5,782,904 A | 7/1998 | White et al. | |
| 5,873,906 A | 2/1999 | Lau et al. | |
| 6,042,605 A | 3/2000 | Martin et al. | |
| 6,270,520 B1 | 8/2001 | Inoue | |
| 6,352,553 B1 | 3/2002 | Van der Burg et al. | |
| 6,352,561 B1 | 3/2002 | Leopold et al. | |

(Continued)

FOREIGN PATENT DOCUMENTS

WO WO2009/148594 12/2009

OTHER PUBLICATIONS

Bungay et al. "Initial Experience With a New Fenestrated Stent Graft" Journal of Vascular Surgery, 2011, pp. 1-7.

*Primary Examiner* — Thomas J Sweet
*Assistant Examiner* — Seema Mathew

(57) ABSTRACT

A circumferentially constraining suture for an endovascular prosthesis having a tubular body and a plurality of stents coupled to the tubular body includes a first thread coupled at a first end to one of the stents and a first thread loop disposed opposite the first end. The first thread extends only partially around a circumference of the tubular body in a radially expanded configuration. A second thread having a second thread loop is interlocked with the first thread loop and extends from the first thread loop around a remainder of the circumference of the tubular body. Pulling the second thread causes the first thread to circumferentially constrain the tubular body to a reduced diameter configuration. A trigger wire inserted through the first thread loop retains the first thread such that the tubular body is in the reduced diameter configuration after removal of the second thread.

18 Claims, 12 Drawing Sheets

(56) References Cited

U.S. PATENT DOCUMENTS

| | | |
|---|---|---|
| 6,361,637 B2 | 3/2002 | Martin et al. |
| 6,471,722 B1 | 10/2002 | Inoue |
| 6,520,986 B2 | 2/2003 | Martin et al. |
| 6,524,335 B1 | 2/2003 | Hartley et al. |
| 6,551,350 B1 | 4/2003 | Thornton et al. |
| 7,131,991 B2 | 11/2006 | Zarins et al. |
| 7,306,623 B2 | 12/2007 | Watson |
| 7,413,573 B2 | 8/2008 | Hartley et al. |
| 7,438,721 B2 | 10/2008 | Doig et al. |
| 7,537,606 B2 | 5/2009 | Hartley et al. |
| 7,678,141 B2 | 3/2010 | Greenan et al. |
| 7,682,380 B2 | 3/2010 | Thornton et al. |
| 7,736,571 B2 | 6/2010 | Trapp |
| 7,823,267 B2* | 11/2010 | Bolduc .................. 29/525.01 |
| 7,867,270 B2 | 1/2011 | Hartley et al. |
| 7,955,374 B2 | 6/2011 | Erickson et al. |
| 8,926,686 * | 1/2015 | King ........................ 623/1.13 |
| 2001/0037142 A1* | 11/2001 | Stelter et al. .............. 623/1.13 |
| 2005/0182476 A1* | 8/2005 | Hartley et al. ............ 623/1.11 |
| 2006/0095119 A1 | 5/2006 | Bolduc |
| 2006/0142836 A1* | 6/2006 | Hartley et al. ............ 623/1.11 |
| 2007/0032862 A1* | 2/2007 | Weber et al. ............. 623/1.34 |
| 2007/0043425 A1* | 2/2007 | Hartley et al. ............ 623/1.12 |
| 2007/0055360 A1 | 3/2007 | Hanson et al. |
| 2007/0208256 A1 | 9/2007 | Marilla |
| 2007/0225797 A1* | 9/2007 | Krivoruhko .............. 623/1.35 |
| 2007/0233220 A1 | 10/2007 | Greenan |
| 2007/0244547 A1 | 10/2007 | Greenan |
| 2007/0250152 A1 | 10/2007 | Xiao et al. |
| 2008/0294234 A1* | 11/2008 | Hartley et al. ............ 623/1.12 |
| 2009/0204202 A1 | 8/2009 | Dierking et al. |
| 2009/0216308 A1* | 8/2009 | Hartley .................... 623/1.11 |
| 2010/0049313 A1* | 2/2010 | Alon et al. ............... 623/2.11 |
| 2010/0286757 A1* | 11/2010 | Petersen et al. .......... 623/1.13 |
| 2011/0087320 A1* | 4/2011 | Bolduc et al. ............ 623/1.35 |
| 2011/0118816 A1 | 5/2011 | Jensen et al. |
| 2011/0125244 A1* | 5/2011 | Roeder et al. ............ 623/1.11 |
| 2011/0125249 A1 | 5/2011 | Jensen et al. |
| 2011/0190868 A1 | 8/2011 | Ducke et al. |
| 2011/0264192 A1* | 10/2011 | Hartley et al. ............ 623/1.13 |
| 2012/0035714 A1 | 2/2012 | Ducke et al. |
| 2012/0046728 A1* | 2/2012 | Huser et al. .............. 623/1.13 |
| 2012/0172965 A1* | 7/2012 | Kratzberg et al. ........ 623/1.12 |
| 2012/0259406 A1* | 10/2012 | Schreck et al. ........... 623/1.27 |
| 2012/0277848 A1* | 11/2012 | Roeder et al. ............ 623/1.13 |
| 2013/0046371 A1* | 2/2013 | Greenberg et al. ....... 623/1.11 |
| 2013/0116773 A1* | 5/2013 | Roeder et al. ............ 623/1.15 |
| 2013/0166015 A1* | 6/2013 | Roeder .................... 623/1.13 |
| 2014/0148888 A1* | 5/2014 | Barrand .................... 623/1.2 |
| 2014/0148895 A1* | 5/2014 | King ........................ 623/1.13 |
| 2014/0180378 A1* | 6/2014 | Roeder .................... 623/1.11 |
| 2014/0277338 A1* | 9/2014 | Kolbel et al. ............ 623/1.11 |
| 2015/0012080 * | 1/2015 | Barrand .................... 623/1.13 |

* cited by examiner

CIRCUMFERENTIALLY CONSTRAINING SUTURES FOR A STENT-GRAFT

FIELD OF THE INVENTION

This invention relates generally to endoluminal medical devices and procedures, and more particularly to an endoluminal prosthesis or stent-graft having circumferentially constraining sutures to circumferentially constrain the stent-graft for a partial deployment of the stent-graft.

BACKGROUND

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, which could include renal, superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

For patients with aneurysms of the aorta, surgery to replace the aorta may be performed where a portion of the aorta is replaced with a fabric substitute in an operation that uses a heart-lung machine. In such a case, the aneurysmal portion of the aorta is removed or opened and a substitute lumen is sewn across the aneurysmal portion to span it. Such surgery is highly invasive, requires an extended recovery period and, therefore, cannot be performed on individuals in fragile health or with other contraindicative factors.

When aneurysms are near branch vessels or extend into branch vessels, stent-grafts are used with fenestrations, external couplings, or other means for branch stent-grafts to be deployed into the branch vessels. The location of such fenestrations or external couplings may be critical so as not to block branch vessels. Further, when aneurysms are near branch vessels, the "landing zone" for the stent-graft may be limited such that accurate placement of the stent-graft is critical. Thus, it is desirable to be able to accurately position the stent-graft. However, stents of the stent-graft are normally designed to expand to a size larger than the target vessel to ensure apposition against the vessel wall. Thus, re-positioning the stent-graft after deployment is difficult. It is thus desirable to partially deploy the stent-graft to a diameter larger than the delivery catheter diameter, but smaller than the fully deployed diameter to enable re-positioning of the stent-graft.

Further, when aneurysms are located near branch vessels, it may be desirable to deploy the stent-graft to a diameter smaller than the fully deployed diameter in the main vessel in order to perform various actions to cannulate the branch vessels prior to completely deploying the stent-graft. Partially deploying the stent-graft allows for space outside of the stent-graft within the main vessel to perform such actions.

Devices to maintain stent-grafts in a partially deployed configuration after release from a catheter have been contemplated. However, with current devices, the stent-graft may jump out of position when the stent-graft is deployed. Accordingly, it would be desirable to minimize any movement of the stent-graft when fully deploying the stent graft by releasing the circumferentially constraining sutures.

SUMMARY OF THE INVENTION

Embodiments hereof relate to circumferentially constraining sutures for a stent-graft. The stent-graft includes a tubular body of a graft material and a plurality of stents coupled to the tubular body. The circumferentially constraining suture in a reduced diameter configuration includes a first end attached to one of the stent and extending circumferentially around a complete circumference of the tubular body, with a loop of the circumferentially constraining suture disposed opposite the first end being coupled to a trigger wire extending in a longitudinal direction along the tubular body. In a deployed configuration, the trigger wire is disengaged from the loop such that the stent radially expands and the circumferentially constraining suture extends only partially around the circumference of the tubular body.

Embodiments hereof also relate to circumferentially constraining sutures for stent-grafts. The stent-graft includes a tubular body of a graft material and a plurality of stents coupled to the tubular body. The circumferentially constraining suture includes a first thread coupled at a first end to the tubular body or one of the stents and having a first thread loop disposed opposite the first end, the first thread extending only partially around a circumference of the tubular body when the stent-graft is in a radially expanded configuration. The circumferentially constraining suture further includes a second thread having a second thread loop interlocked with the first thread loop, the second thread extending from the first thread loop around a remainder of the circumference of the tubular body. The circumferentially constraining suture is configured such that pulling the second thread causes the first thread to circumferentially constrain the tubular body such that the tubular body constricts to a reduced diameter configuration.

Embodiments hereof also relate to a method for temporarily reducing the diameter of at least a portion of a self-expanding stent-graft. The stent-graft includes a tubular body of a biocompatible graft material and a plurality of self-expanding stents. A first thread having a first thread loop and a second thread having a second thread loop are interlocked. The first thread at a first end opposite the first thread loop is attached to one of the stents. The first thread is extended around a first portion of the circumference of the tubular body and the second thread around is extended from the first thread around a second portion of the circumference of the tubular body. The second thread is pulled to cause the first loop of the first thread to move along the second portion of the circumference to reduce the diameter of the tubular body. A trigger wire is inserted longitudinally along the tubular body and through the first loop to retain the tubular body in a reduced diameter configuration after the second thread is removed.

DETAILED DESCRIPTION

Figure 1:
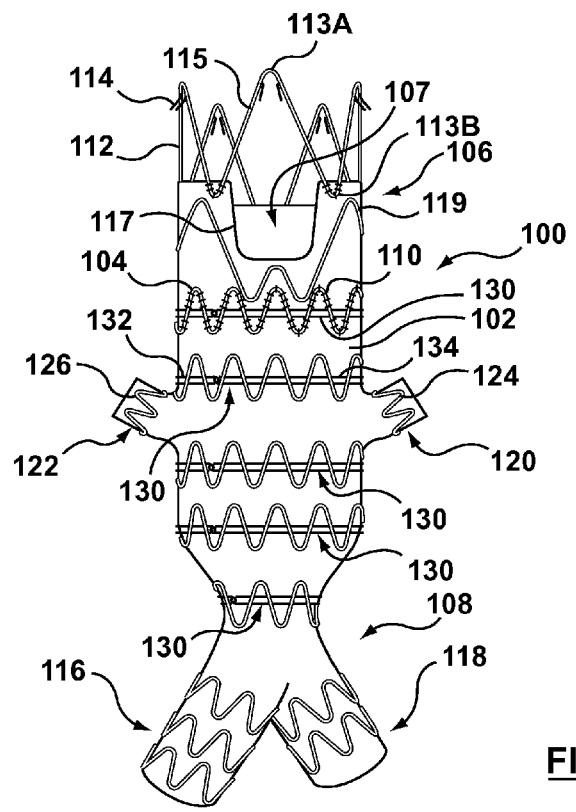
FIG. 1 is a perspective view of a main vessel stent-graft including circumferentially constraining sutures according to an embodiment hereof, wherein the main vessel stent-graft in radially expanded configuration.

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis proximal is the portion nearer the heart by way of blood flow path while distal is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as aorta, the invention may also be used in any other blood vessels and body passageways where it is deemed useful. Furthermore, there is no intention to be bound by any expressed or implied theory presented in the preceding technical field, background, brief summary or the following detailed description.

With reference to FIGS. 1-7, a self-expanding main vessel endovascular prosthesis or stent-graft 100 is configured for placement in a vessel such as the abdominal aorta. In the particular embodiment shown, main vessel stent-graft 100 is a bifurcated stent-graft configured to treat short-neck infrarenal, juxtarenal, and/or suprarenal aneurysms in a wide range of patient anatomies. However, the invention is not so limited and may also be used for stent-grafts for use in other areas and without all of the features described below.

FIG. 1 illustrates a perspective view of main vessel stent-graft 100 in a radially expanded configuration prior to placement within a delivery catheter. In this application, the terms "radially expanded configuration" and "deployed configuration" are used to describe the stent-graft when it is not in a delivery catheter and without circumferentially constraining sutures (described below) restricting the expansion of the stents of the stent-graft prosthesis. However, it would be recognized by those skilled in the art that the "radially expanded configuration" and the "deployed configuration" may not be exactly the same diameter because at least some of the stents of the stent-graft may be oversized to ensure a tight seal of the stent-graft to the vessel wall. Accordingly, the "deployed configuration" may be smaller than the "radially expanded configuration" in practice due to the vessel wall restricted expansion of the stents. However, for purposes of this application, the terms generally mean that there are no outside forces (other than the vessel wall) restricting expansion of the stent-graft prosthesis. Stent-graft 100 includes a generally tubular or cylindrical graft or body 102 that defines a lumen 107 and has a first edge or end 106 and a second edge or end 108. Tubular graft 102 may be formed from any suitable graft material, for example and not limited to, a low-porosity woven or knit polyester, DACRON material, expanded polytetrafluoroethylene, polyurethane, silicone, ultra high molecular weight polyethylene, or other suitable materials. In another embodiment, the graft material could also be a natural material such as pericardium or another membranous tissue such as intestinal submucosa. A plurality of stents 104 are coupled to graft 102. Stents 104 may be coupled to graft 102 by stitching 110 or by other means known to those skilled in the art. In the embodiment shown, stents 104 are coupled to an outside surface of graft 102, but stents 104 may alternatively be coupled to an inside surface of graft 102.

An anchor stent 112 is coupled to graft 102 adjacent first end 106 of graft 102. Anchor stent 112 is a radially-compressible ring or scaffold that is operable to self-expand into apposition with an interior wall of a body vessel (not shown). Anchor stent 112 is constructed from a self-expanding or spring material, such as nitinol, and is a sinusoidal patterned ring including a plurality of crowns or bends 113A, 113B and a plurality of struts or straight segments 115 with each crown being formed between a pair of opposing struts. Anchor stent 112 is coupled to the graft material so as to have a first or proximal-most set of crowns 113A that extend outside of or beyond first edge 106 of graft 102 in an open web or free-flow configuration and a second or opposing set of crowns 113B that is coupled to first edge 106 of tubular graft 102. Crowns 113B are coupled to tubular graft 102 by stitches or other means known to those of skill in the art. In the embodiment shown, crowns 113B are coupled to an outside surface of tubular graft 102. However, crowns 113B may alternatively be coupled to an inside surface of tubular graft 102. Unattached or free crowns 113A may include barbs 114 for embedding into and anchoring into vascular tissue when stent-graft prosthesis 100 is deployed in situ. In an embodiment, anchor stent 112 may be the Endurant II™ suprarenal stent, manufactured by Medtronic, Inc., of Minneapolis, Minn.

A scallop 117 cut out or removed from graft 102 at proximal or first end 106. Scallop 117 is an open-topped fenestration. When deployed in situ, scallop 117 is positioned within the aorta distal of the superior mesenteric artery (SMA) and extends around and/or frames the ostium of the SMA. In short-neck infrarenal, juxtarenal, and/or suprarenal aneurysms, first edge 106 of tubular graft 102 is deployed within the abdominal aorta at or near the superior mesenteric artery (SMA). In order to avoid blockage of blood flow into the superior mesenteric artery (SMA), stent-graft 100 is positioned or oriented within the abdominal aorta such that scallop 117 is positioned around the ostium of the superior mesenteric artery (SMA) and the graft material of tubular graft 102 does not occlude the ostium of the SMA. The presence of scallop 117 for the SMA allows for main vessel stent-graft 100 to deploy and seal against a sufficient length, i.e., greater than 10 mm, of healthy or non-aneurysmal tissue distal to the SMA for patients suffering from short-neck infrarenal, juxtarenal, and/or suprarenal aneurysms.

A seal stent 119 is coupled to graft 102 at first end 106. Seal stent 119 is configured to accommodate scallop 117. Seal stent 119 is a radially-compressible ring or scaffold that is coupled to tubular graft 102 for supporting the graft material and is operable to self-expand into apposition with an interior wall of a blood vessel (not shown). Seal stent 119 is constructed from a self-expanding or spring material, such as nitinol, and is a sinusoidal patterned ring including a plurality of crowns or bends and a plurality of struts or straight segments with each crown being formed between a pair of opposing struts. Seal stent 119 is coupled to tubular graft 102, immediately distal of first end 106 thereof and distal of anchor stent 112. Seal stent 119 is coupled to tubular graft 102 by stitches or other means known to those of skill in the art. In the embodiment shown, seal stent 119 is coupled to an outside surface of tubular graft 102, but seal stent 119 may alternatively be coupled to an inside surface of tubular graft 102. Seal stent 119 includes at least two struts that are lengthened or elongated with respect to the remaining struts to accommodate scallop 117.

In the embodiment shown, stent-graft 100 includes a first tubular leg or extension 116 and a second tubular leg or extension 118, each extending from second end 108. Legs 116, 118 define lumens that are in fluid communication with lumen 107 of tubular graft 102. In an embodiment, legs 116, 118 are integrally formed with tubular graft 102 as a unitary graft component and thus are formed from the same material as tubular graft 102. In another embodiment, legs 116, 118 may be formed separately from tubular graft 102 and coupled thereto. In the embodiment shown, legs 116, 118 are of equal length and are oriented anterior and posterior within the abdominal aorta when deployed in the abdominal aorta.

Stent-graft 100 also includes couplings 120, 122 for connecting stent-graft 100 to branch vessel prostheses (not shown) to accommodate the left and right renal arteries, respectively. Tubular graft 102 includes opposing fenestrations or openings formed through a sidewall of the graft material. Couplings 120, 122 are disposed on an outside surface of main vessel stent-graft 100 corresponding to openings in tubular graft 102. Couplings 120, 122 may be generally cylindrically shaped or frustoconically shaped. Couplings 120, 122 include coupling graft material. The graft material of couplings 120, 122 may be the same type of graft material as the graft material of tubular graft 102 or it may be a different material. Also, in the embodiment shown, couplings 120, 122 are separate components that are attached to tubular graft 102. However, it would be understood by those of ordinary skill in the art that couplings 120, 122 may be formed as a continuation of tubular graft 102. Couplings 120, 122 include self-expanding support stents or sinusoidal rings 124, 126, respectively, coupled to the coupling graft material. Support stents 124, 126 are constructed from a self-expanding or spring material, such as nitinol, and is a sinusoidal patterned ring including a plurality of crowns or bends and a plurality of struts or straight segments with each crown being formed between a pair of opposing struts. In an embodiment, support stents 124, 126 are four peak stents and thus include eight crowns, although it will be apparent to one of ordinary skill in the art that the support stent may include more or less crowns. Other embodiments of couplings 124, 126 may be used as would be understood by those skilled in the art.

Although stent-graft 100 has been described generally above, more details of stent-graft 100 may be found in U.S. patent application Ser. Nos. 13/458,209 and 13/458,242 to Coghlan et al., filed Apr. 27, 2012 now published as U.S. Pub. Nos. 2013/0289701 A1 and 2013/0289702 A1), herein incorporated by reference in their entirety. Further, although stent-graft 100 has been described with the particular features described above, the circumferentially constraining sutures described below may be used with any stent-graft where it is desirable to have a staged deployment of the stent-graft prosthesis.

As described above, FIG. 1 shows stent-graft 100 in a radially expanded configuration prior to placement within a delivery catheter for delivery to a treatment site. In the embodiment shown, five circumferentially constraining sutures 130 are disposed around stent-graft 100. Circumferentially constraining sutures 130, when utilized as described in more detail below, reduce the diameter of stent-graft prosthesis 100 by about 40 to 70 percent from the radially expanded configuration. However, stent-graft 100 in the reduced diameter configuration has a diameter about 40 to 50 percent larger than in a delivery configuration wherein stent-graft 100 is disposed within a sleeve of a delivery catheter. Those of ordinary skill in the art would recognize that by adjusting the length of the threads of the circumferentially constraining sutures, as described in more detail below, the reduction in the diameter of stent-graft prosthesis by the circumferentially constraining sutures may be varied outside of the ranges noted above.

In the embodiment shown, circumferentially constraining sutures 130 are disposed around the graft material of tubular graft 102 adjacent five of stents 104. As explained in more detail below, anchor stent 112 is held by a tip capture mechanism during delivery and partial deployment of stent-graft 100. The tip capture mechanism holds proximal-most crowns 113A of anchor stent 112 in a reduced diameter configuration after retraction of the outer sheath or sleeve covering stent-graft 100, as known to those skilled in the art. Thus, anchor stent 112 and seal stent 119 do not include circumferentially constraining sutures because they do not fully deploy due to the tip capture mechanism. However, as would be understood by those skilled in the art, more or less circumferentially constraining sutures 130 may be utilized depending on the number of stents 104 coupled to tubular graft 102, the particular application and procedure, and the locations where it is desirable to have a reduced diameter.

Figure 2:
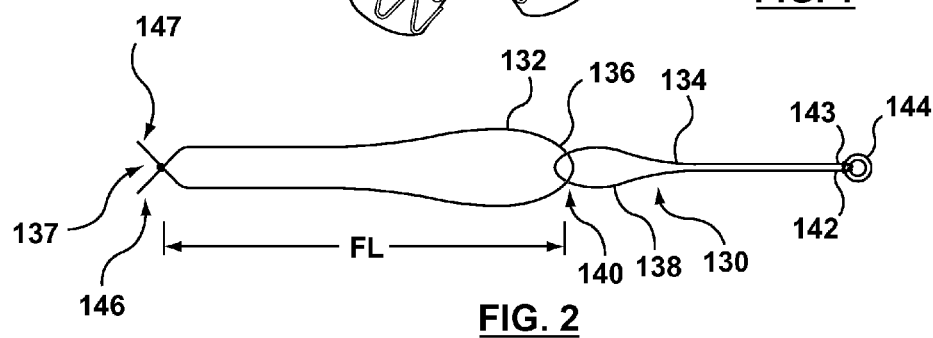
FIG. 2 is a schematic illustration of a circumferentially constraining suture.
Figure 2A:
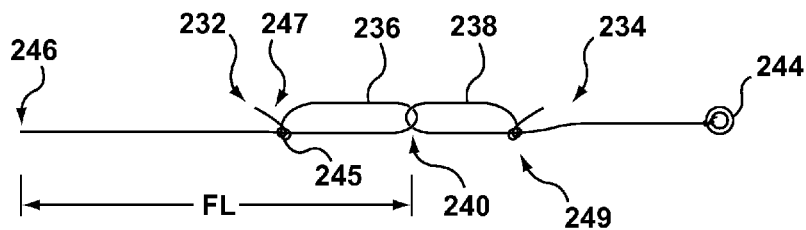

Each circumferentially constraining suture 130 comprises a first thread or string 132 interlocked with a second thread or string 134 at interlocking location 140. First thread 132 is formed into a first thread loop 136 by having a first end 146 and a second end 147 of first thread 132 disposed tied to each other at knot 137, as shown in FIG. 2. Essentially, first thread 132 is folded back at approximately a mid-point thereof to form a first thread loop 136. First thread 132 has a first thread length FL that is less than the circumference of stent-graft 100. In particular, first thread length FL may be between 30% and 60% of the circumference of stent-graft 100. Similarly, second thread 134 is folded back at approximately a mid-point thereof to form a second thread loop 138, as shown in FIG. 2. As explained above, first thread length FL may be shorter to make the reduced diameter smaller and first thread length FL may be longer to make the reduced diameter larger. First thread loop 136 and second thread loop 138 are interlocked with each other at 140 as shown in FIG. 2. As also shown in FIG. 2, ends 142 and 143 of second thread 134 disposed opposite second thread loop 138 are tied or otherwise attached to a pull tab 144. Pull tab 144 as shown is a circular, donut shaped tab with ends 142, 143 of second thread 134 tied to pull tab 144. However, those of ordinary skill in the art would recognize that other pull tabs may be used, or a large knot tied in ends 142, 143 may function as a pull tab. Further, those of ordinary skill in the art would recognize that other ways of forming first and second threads with interlocked first and second thread loops may be used. For example, and not by way of limitation, FIG. 2A shows first end 246 of first thread 232 that may be attached to strut 105 (see FIG. 3C described below), and second end 247 may form a first thread loop 232 by forming a loop and tying second end 247 to first thread 232 and 245. Similarly, one end 242 of second thread 234 may be tied to pull tab 244 and the other end 243 of second thread 234 may form a loop 238 and be tied to second thread 234 at 245. Other ways of forming first and second thread loops may be used, as known to those skilled in the art. First thread 132, 232 and second thread 134, 234 may be monofilament or braided and formed of polyester, ultra high molecular weight polyethelene (UHMWPE), polypropylene, or other alternate thread materials known to those skilled in the art.

Figure 3:
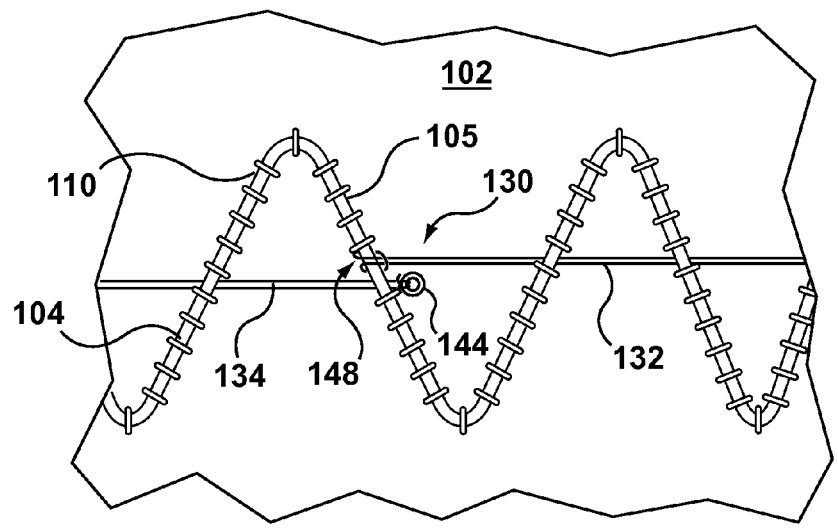
FIG. 3 is zoomed in view of a portion of the stent-graft prosthesis of FIG. 1 where an end of a first thread of a circumferentially constraining suture is attached to a stent and an end of a second thread of the circumferentially constraining suture exits the stent.
Figure 4:
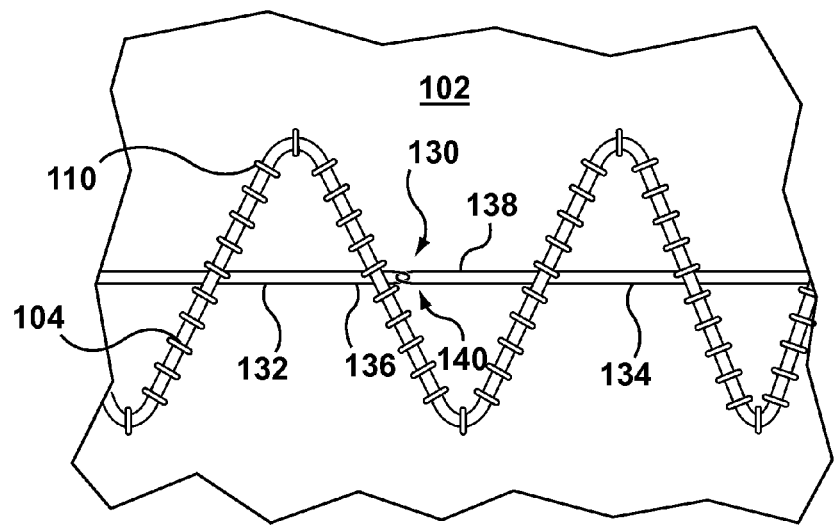
FIG. 4 is zoomed in view of a portion of the stent-graft of FIG. 1 where the first thread and the second thread are interlocked.
Figure 3A:
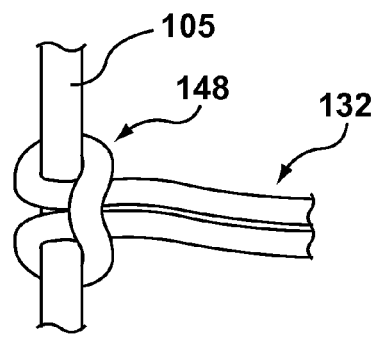
Figure 3B:
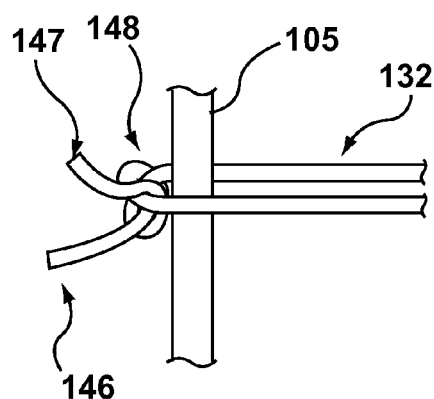
Figure 3C:
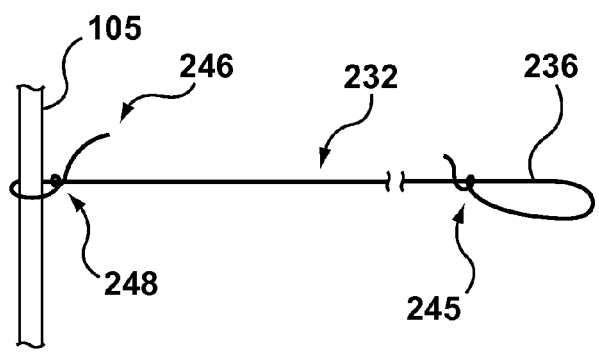

In the embodiment shown, first and second ends 146, 147 of first thread 132 are tied to each other to form first thread loop 136, and first thread loop 136 is tied to a strut 105 of a stent 104, as shown in detail in FIG. 3A. First thread 132 then extends between stent 104 and the graft material of body 102, as shown in FIGS. 3 and 4. First thread 132 also extends between stitches 110 which attach stent 104 to the graft material of body 102, thereby keeping first thread 132 from moving longitudinally along stent-graft prosthesis 100. First thread 132 is interlocked with second thread 134, which also extends circumferentially around graft material 102 between the graft material and stent 104, as shown in FIG. 4. Other ways of forming first thread loop 136 and of attaching first thread loop 136 to stent 104 may be utilized, as would be recognized by those skilled in the art. For example, and not by way of limitation, ends 146, 147 of first thread 132 may be tied to each other around strut 105, as shown in FIG. 3B. Further, using the first thread loop 234 shown in FIG. 2A, first end 246 of first thread may be tied around strut 105 at knot 248 and first thread loop 236 is disposed at the opposite end of knot 248 by having second end 247 form loop 236 and then tying second end 247 to first thread 232, as shown in FIG. 3C.

Figure 5:
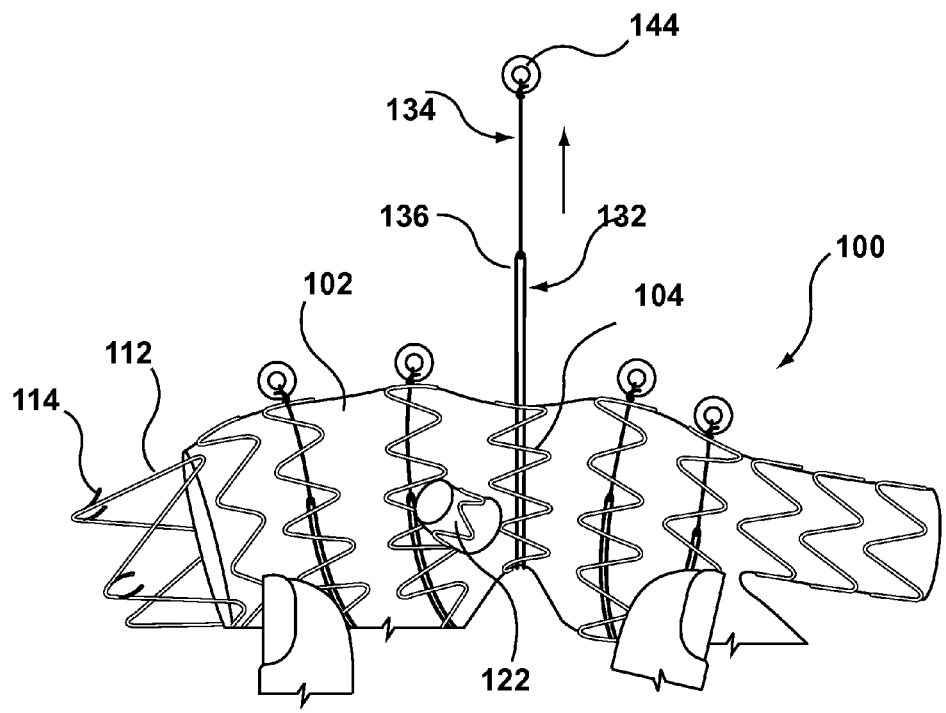
FIG. 5 is a schematic illustration of a circumferentially constraining suture of the stent-graft of FIG. 1 with the second thread pulled to tighten the first thread around the stent-graft.

Circumferentially constraining sutures 130 function to circumferentially constrain stent-graft 100, as will be described with reference to FIGS. 5-7. First, as shown in FIG. 5, second thread 134 is pulled by pulling on pull tab 144. Because first thread 132 is attached to a body stent 104 at an end opposite first thread loop 136, and second thread 134 is disposed between graft 102 and stents 104, pulling second thread 134 causes first thread to continue around the circumference of stent-graft 100, following the path of second thread 134 until the location where pull tab 144 was initially located. At that point, pulling second thread 134 causes first thread to continue following second thread 134, but first thread loop 136 may extend radially away from stent-graft 100, as shown in FIG. 5. Further, because first thread 132 is fixed to a stent 104 at 148, pulling second thread 134 and first thread 132 along with it causes first thread 132 to circumferentially close or tighten or shrink stent-graft 100 in the area of circumferentially constraining suture 130, as also shown in FIG. 5.

Figure 6:
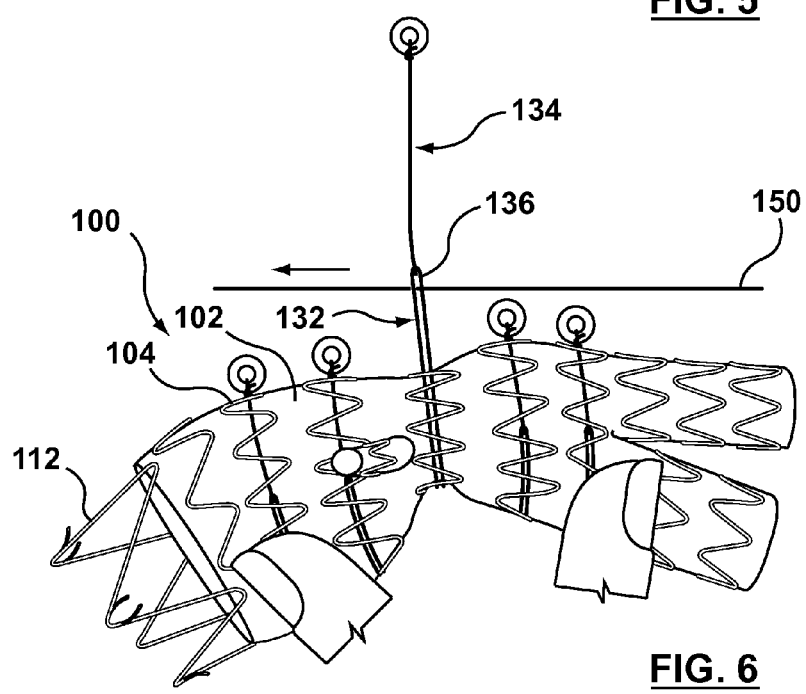
FIG. 6 is a schematic illustration of a trigger wire being inserted through a first thread loop of a circumferentially constraining suture.
Figure 7:
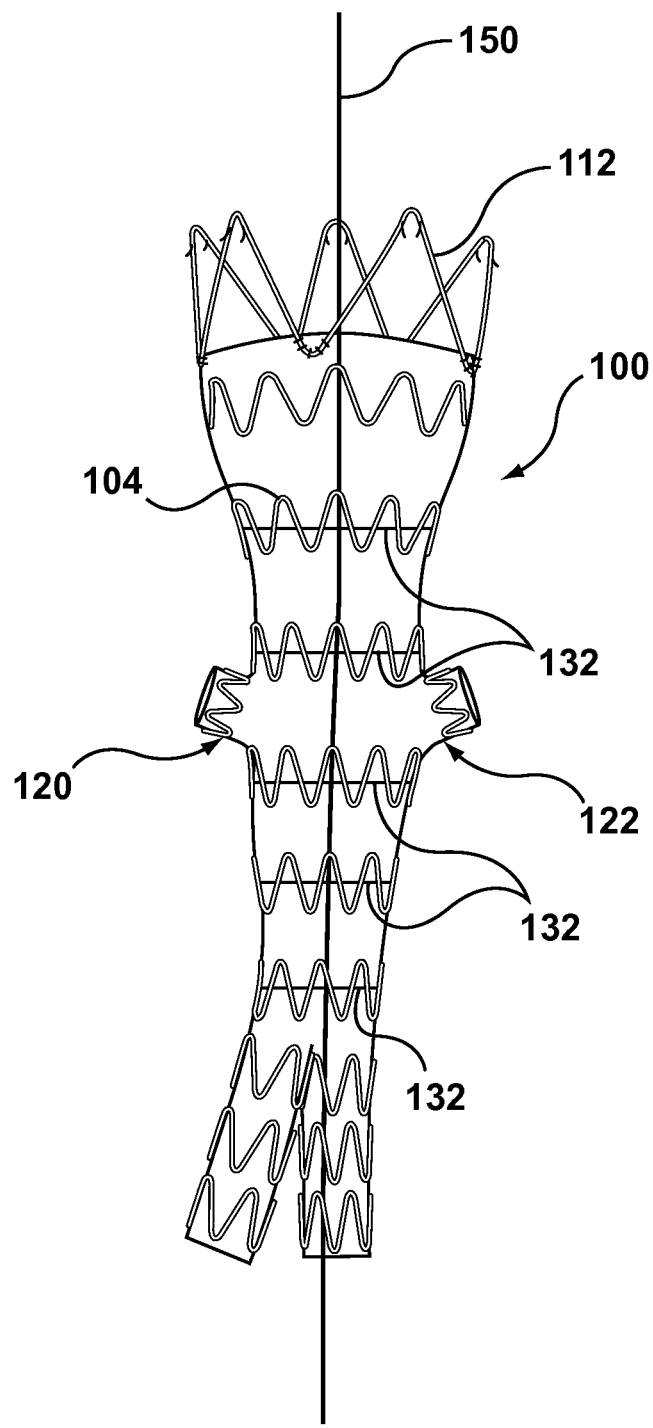
FIG. 7 is a schematic illustration of the stent graft prosthesis of FIG. 1 in a reduced diameter configuration with the trigger wire extending through the first thread loop of each circumferentially constraining suture.

Next, as shown in FIG. 6, a release or trigger wire 150 extending generally longitudinally along stent-graft 100 is inserted through first thread loop 136. The steps of FIGS. 5 and 6 are repeated for each circumferentially constraining suture 130 of stent-graft 100. Preferably, the same trigger wire 150 is used for all the circumferentially constraining sutures, but it is not necessary. Although FIGS. 5 and 6 show the middle circumferentially constraining suture 130, it would be understood that with a single trigger wire 150, it is preferable to proceed from either the proximal-most or the distal-most circumferentially constraining suture 130 and proceed either distally or proximally, respectively, with trigger wire 150 advancing along either distally or proximally, respectively, to engage each first thread loop 136 of each first thread 132.

When each first thread loop 136 of each first thread 132 is engaged by trigger wire 150, each second thread 134 may be removed. This causes the stent 104 associated with the circumferentially constraining suture to try to expand to its radially expanded diameter. However, because trigger wire 150 holds first threaded loop 136 at the location where second thread 134 exited from between graft 102 and the stent 104, and the first thread length FL of first thread 132 is fixed and is less than the circumference of stent-graft 100, trigger wire 150 holds stent-graft 100 in a reduced diameter configuration. It is preferable that pull tab 144 is located adjacent knot 148, as shown in FIG. 3. In other words, it is preferable that when trigger wire 150 holds circumferentially constraining suture 130 such that stent-graft 100 is in the reduced diameter configuration, first thread 132 extends completely around the circumference of stent-graft 100. In such an embodiment, the first thread length FL of first thread 132 determines the amount that the circumferentially constraining suture 130 reduces the diameter of stent-graft 100. Further, in such an embodiment, the circumferentially constraining suture 130 constrains stent-graft 100 around the entire circumference of stent-graft 100, thereby applying equal restraining force around the circumference of the stent-graft to minimize movement of the stent-graft when releasing stent graft prosthesis 100 from the circumferentially constraining sutures 130 by removing the trigger wire 150.

After the trigger wire 150 is disposed through first thread loop 136 of each circumferentially constraining suture 130, second thread 134 can be removed such as by cutting second thread loop 138. This leaves stent-graft 100 in the reduced diameter configuration with trigger wire 150 disposed through each first thread loop 136 of each first thread 132 of each circumferentially constraining suture 130, as shown in FIG. 7. Trigger wire 150 extends within a delivery catheter to a handle of the delivery catheter such that a user may pull trigger wire 150 to release each circumferentially constraining suture 130 such that stent-graft prosthesis 100 may expand to its deployed configuration, as described in more detail below. Trigger wire 150 may be any suitable wire formed of any suitable material. For example, and not by way of limitation, trigger wire may be formed of nitinol, and may have a diameter in the range of 0.010 to 0.014 inch. However, it is understood that different materials and different sizes can be used provided that the trigger wire can perform the functions described herein of holding first thread 132 to maintain the stent-graft in a reduced diameter configuration and of releasing the circumferentially constraining suture by retraction of the trigger wire without excessive force by the user.

Stent-graft 100 can then be disposed within a delivery catheter as known to those skilled in the art. After delivery to a target site and partial deployment of stent-graft prosthesis 100 from a sheath or outer cover of the delivery system, trigger wire 150 may be retracting proximally (i.e., towards the clinician) to release circumferentially constraining sutures 130 and allow stent-graft prosthesis 100 to fully deploy to its radially expanded or deployed configuration, as described in more detail below. With second thread 134 removed from each circumferentially constraining suture 130, only first thread 132 remains. The drawings and description regarding delivery and deployment of the stent-graft 100 may refer to first thread 132 and circumferentially constraining suture 130 interchangeably.

Figure 8:
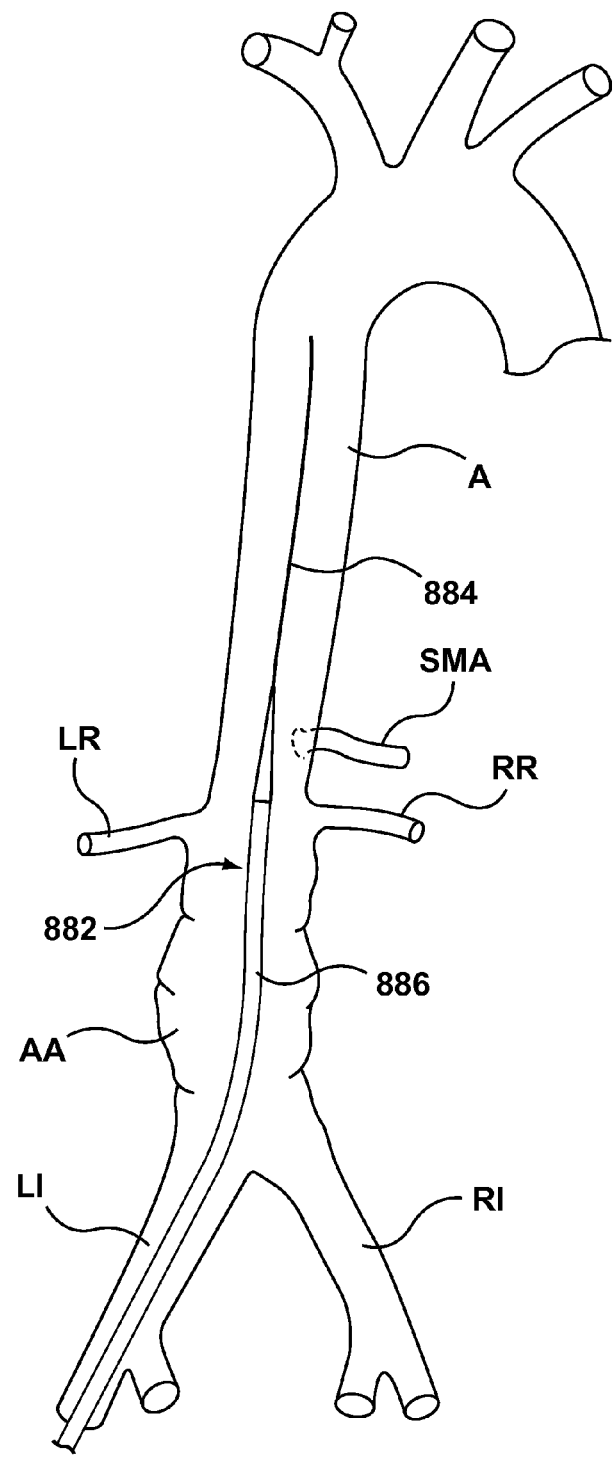
FIGS. 8-14 schematically illustrate a method of delivering the main vessel stent-graft of FIG. 1 to a target site in the abdominal aorta, partial deployment of the stent-graft, and full deployment of the stent-graft after release of the circumferentially constraining sutures.

FIG. 8 shows a main vessel delivery system 882, with main vessel stent-graft 100 compressed therein, advanced over a main vessel guide wire 884 and to the target site in the abdominal aorta A. Guide wire 884 is typically inserted into the femoral artery and routed up through the left iliac artery LI to abdominal aorta, as is known in the art. FIGS. 8-14 show a posterior view of the aorta A and the vessels that branch therefrom. Accordingly, the superior mesenteric artery (SMA), for example, is shown exiting the anterior side of the aorta opposite the posterior side shown in the drawings, and is therefore shown in phantom where blocked by the aorta. FIGS. 8-14 show similar devices as those shown and described in co-pending U.S. patent application Ser. Nos. 13/457,535 and 13/457,544 to Maggard et al., filed Apr. 27, 2012 (now published as U.S. Pub. Nos. 2013/0289696 A1 and 2013/0289693 A1, respectively); U.S. patent application Ser. Nos. 13/457,537 and 13/457,541 to Argentine et al., filed Apr. 27, 2012 (now published as U.S. Pub. Nos. 2013/0289691 A1 and 2013/0289692 A1, respectively); and U.S. patent application Ser. Nos. 13/458,209 and 13/458,242 to Coghlan et al., filed Apr. 27, 2012 (now published as U.S. Pub. Nos. 2013/0289701 A1 and 2013/0289702 A1), herein incorporated by reference in their entirety. However, in the above-identified applications, the views of the delivery and deployment of the stent-graft prosthesis are anterior views of the aorta. Delivery system 882 is fully described in co-pending U.S. patent application Ser. Nos. 13/457,535 and 13/457,544 to Maggard et al., filed Apr. 27, 2012 (now published as U.S. Pub. Nos. 2013/0289696 A1 and 2013/0289693 A1, respectively); and U.S. patent application Ser. Nos. 13/457,537 and 13/457,541 to Argentine et al., filed Apr. 27, 2012 (now published as U.S. Pub. Nos. 2013/0289691 A1 and 2013/0289692 A1, respectively), herein incorporated by reference in their entirety. Main vessel stent-graft prosthesis 100 is mounted on a catheter shaft 988 (see FIG. 9) of the delivery system and an outer delivery sheath 886 of the delivery system covers and restrains main vessel stent-graft prosthesis 100 in a radially compressed delivery configuration for delivery thereof. As will be understood by those of ordinary skill in the art, delivery system 882 may include a tip capture mechanism (not shown) which engages the proximal-most set of crowns of anchor stent 112 until retraction of the tip capture mechanism releases the proximal-most set of crowns for final deployment of main vessel stent-graft prosthesis 100.

Figure 9:
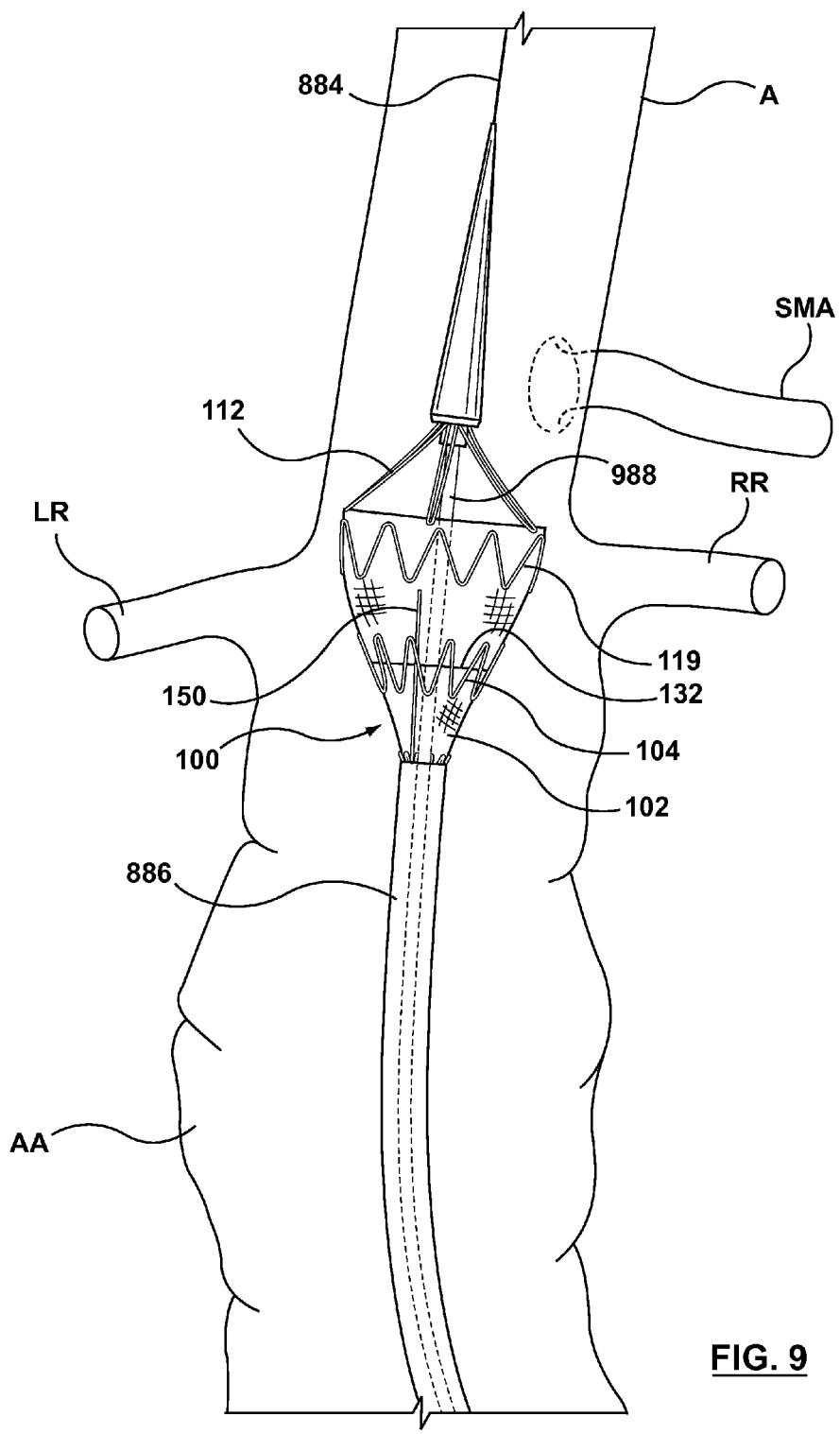

FIG. 9 illustrates a first or initial step to deploy main vessel stent-graft prosthesis 100 in which outer delivery sheath 886 of delivery system 882 is retracted to release or uncover a proximal end portion of main vessel stent-graft prosthesis 100. When first released from the delivery system, the proximal end portion may be positioned such that scallop 117 (not shown in FIG. 9) is below the target site of the superior mesenteric artery (SMA). The proximal-most set of crowns of anchor stent 112 is captured or restrained by the tip capture mechanism of delivery system 882. Delivery sheath 886 is retracted to expose at least seal stent 119. In the embodiment of FIG. 9, delivery sheath 886 is shown as retracted to expose a body stent 104.

As described in co-pending U.S. patent application Ser. Nos. 13/457,535 and 13/457,544 to Maggard et al., filed Apr. 27, 2012 (now published as U.S. Pub. Nos. 2013/0289696 A1 and 2013/0289693 A1, respectively); U.S. patent application Ser. Nos. 13/457,537 and 13/457,541 to Argentine et al., filed Apr. 27, 2012 (now published as U.S. Pub. Nos. 2013/0289691 A1 and 2013/0289692 A1, respectively); and U.S. patent application Ser. Nos. 13/458,209 and 13/458,242 to Coghlan et al., filed Apr. 27, 2012 (now published as U.S. Pub. Nos. 2013/0289701 A1 and 2013/0289702 A1), previously incorporated by reference in their entirety, the superior mesenteric artery (SMA) is cannulated and the main vessel stent-graft 100 is repositioned to align scallop 117 with the superior mesenteric artery (SMA). The terms "cannulation" and "cannulate" are used herein with reference to the navigation of a guidewire and guide catheter into a target vessel.

Figure 10:
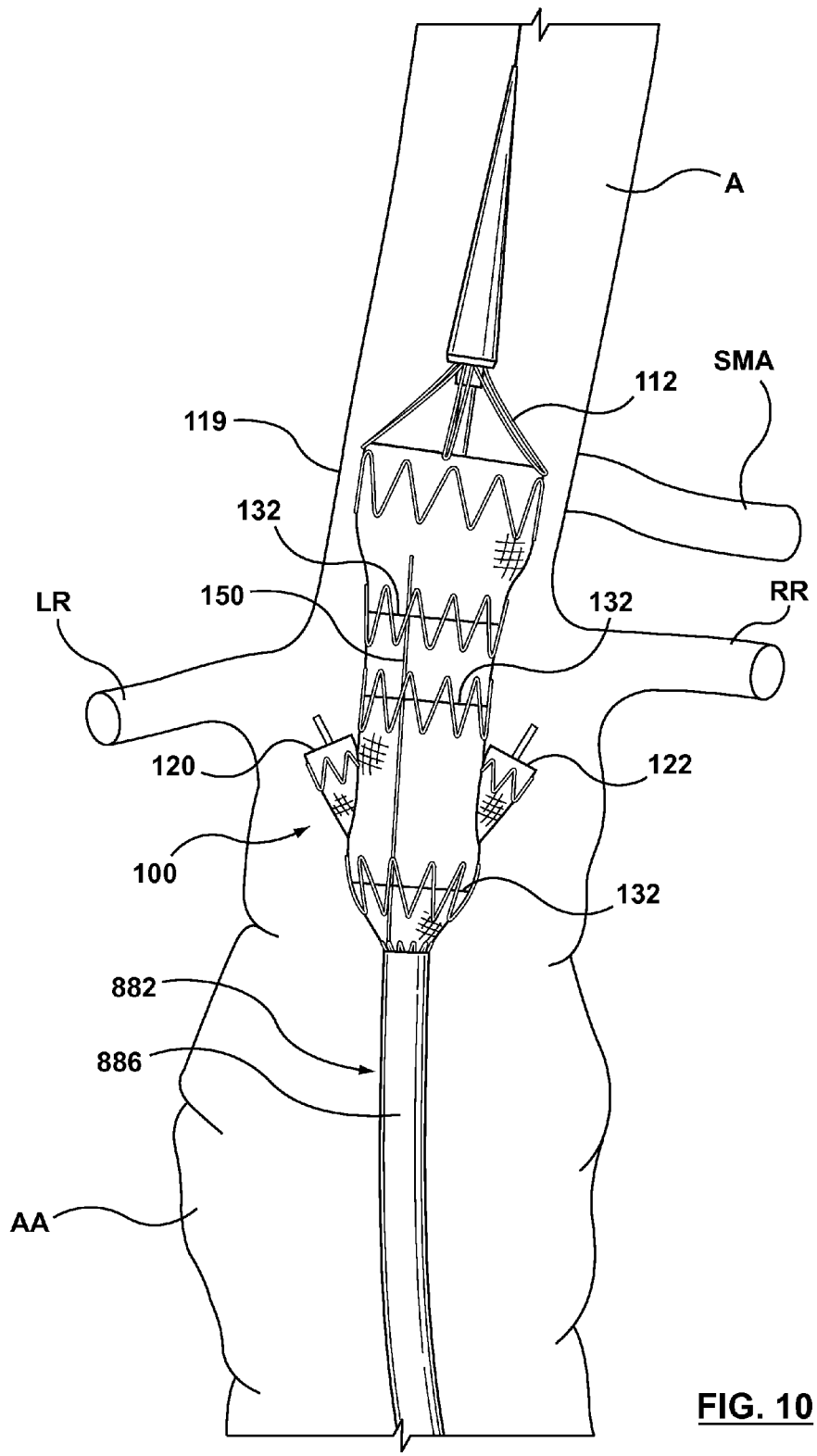

With the proximal end portion of main vessel stent-graft 100 now positioned as desired, delivery sheath 886 is shown retracted in FIG. 10 to expose at least couplings 120, 122 of main vessel stent-graft prosthesis 100. Anchor stent 112 is still captured or restrained by the tip capture mechanism of delivery system 882 such that the proximal end portion of stent-graft 100 does not fully deploy. Further, first threads 132 of circumferentially constraining sutures 130 prevent the stent-graft prosthesis 100 from fully deploying in the areas that have been released from sheath 886. These areas radially expand from the delivery configuration to a reduced diameter configuration that is radially larger than the delivery configuration but 30 to 60% smaller in diameter than the deployed configuration, as explained above.

Figure 11:
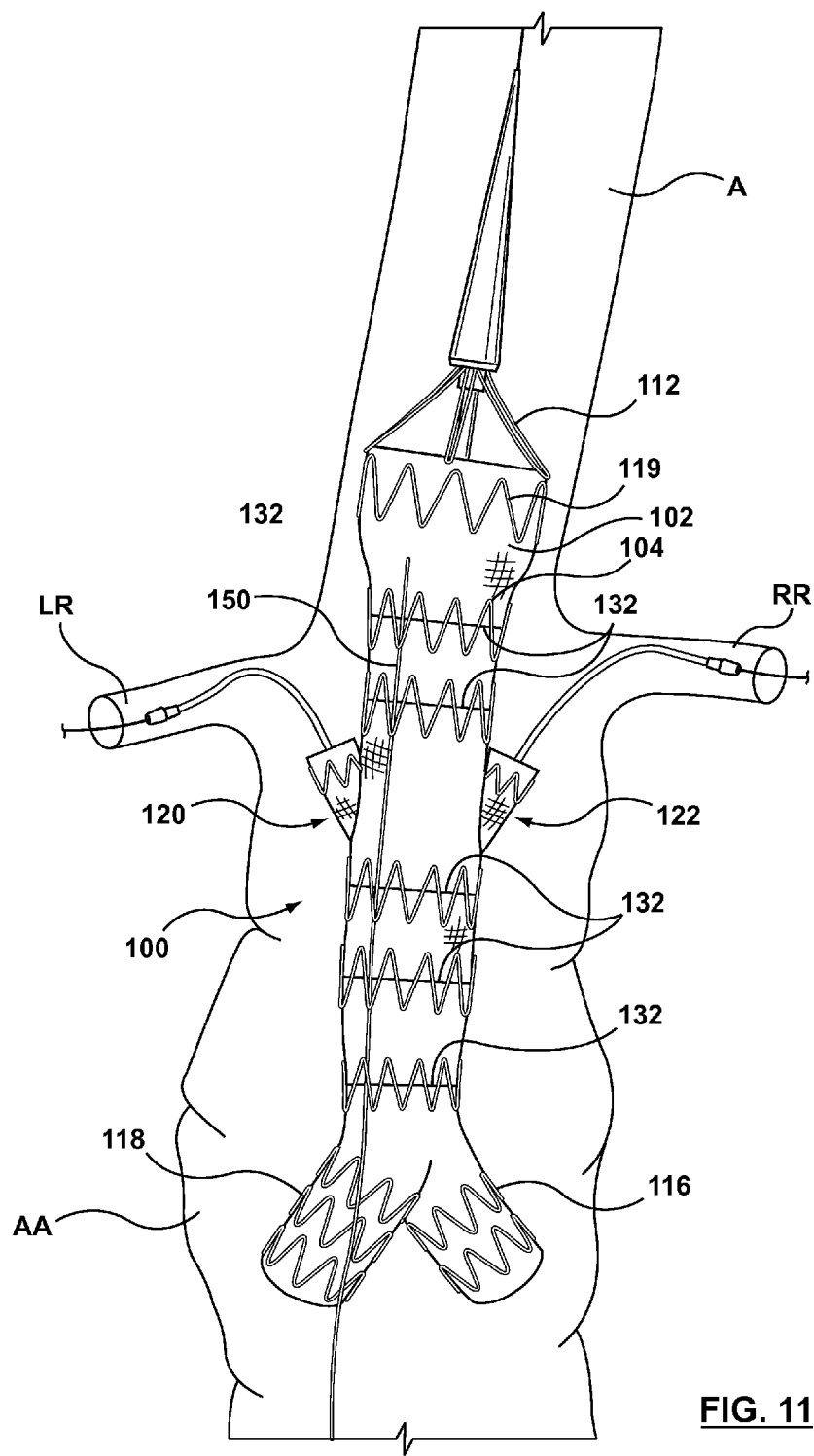

The renal arteries, right renal artery RR and left renal artery LR, are then cannulated, as described in co-pending U.S. patent application Ser. Nos. 13/457,535 and 13/457,544 to Maggard et al., filed Apr. 27, 2012 (now published as U.S. Pub. Nos. 2013/0289696 A1 and 2013/0289693 A1, respectively); U.S. patent application Ser. Nos. 13/457,537 and 13/457,541 to Argentine et al., filed Apr. 27, 2012 (now published as U.S. Pub. Nos. 2013/0289691 A1 and 2013/0289692 A1, respectively); and U.S. patent application Ser. Nos. 13/458,209 and 13/458,242 to Coghlan et al., filed Apr. 27, 2012 (now published as U.S. Pub. Nos. 2013/0289701 A1 and 2013/0289702 A1), previously incorporated by reference in their entirety. The renal arteries are cannulated while sheath 886 is partially retracted as shown in FIG. 10. After the renal arteries have been cannulated, the sheath 886 is fully retracted to release stent-graft 100 from sheath 886 and the branch vessel prosthesis delivery systems are advanced into the renal arteries. This leaves main vessel stent-graft 100 partially deployed in a reduced diameter configuration due to first threads of circumferentially constraining sutures 130, as shown in FIG. 11.

Figure 12:
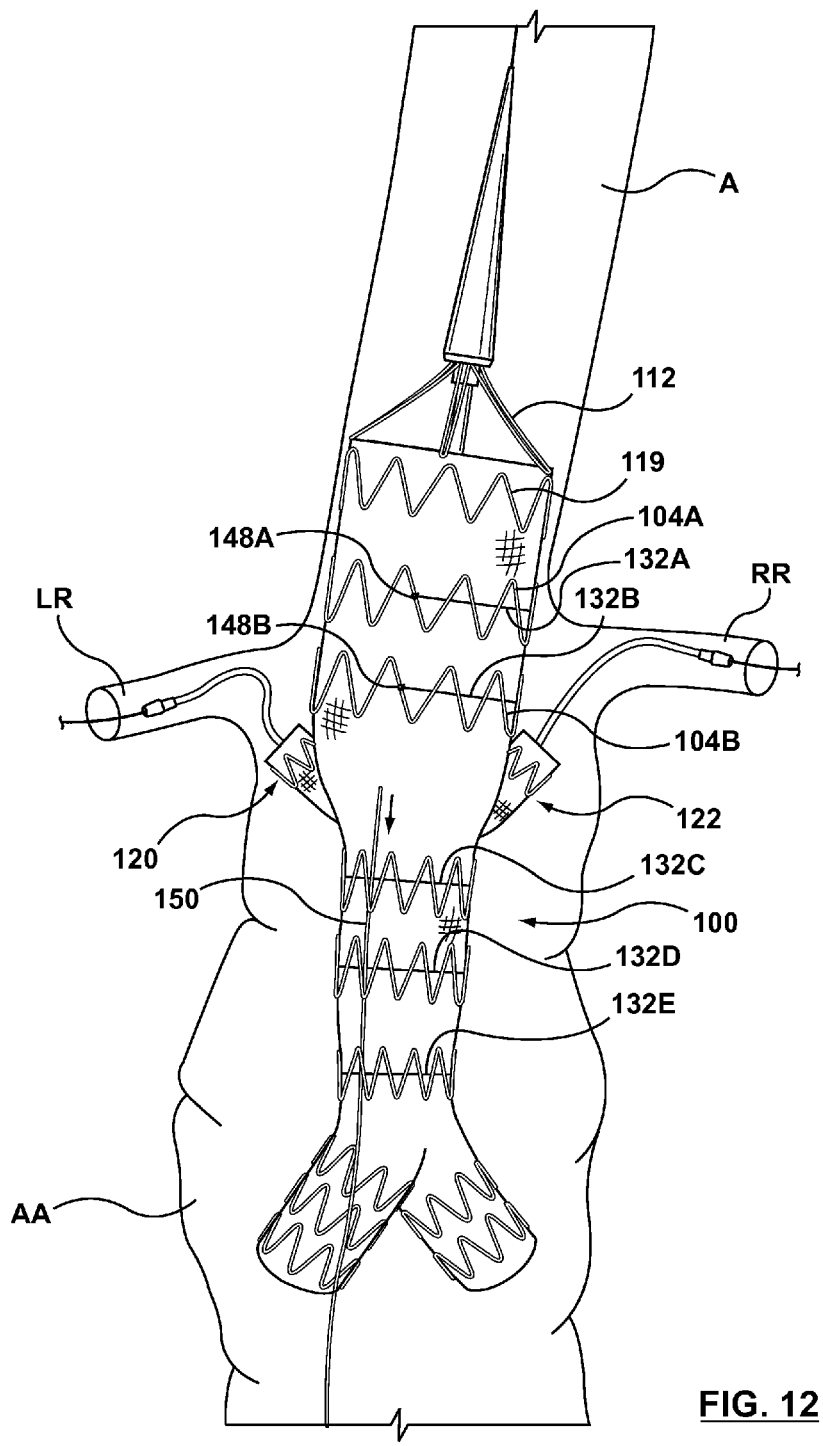
Figure 13:
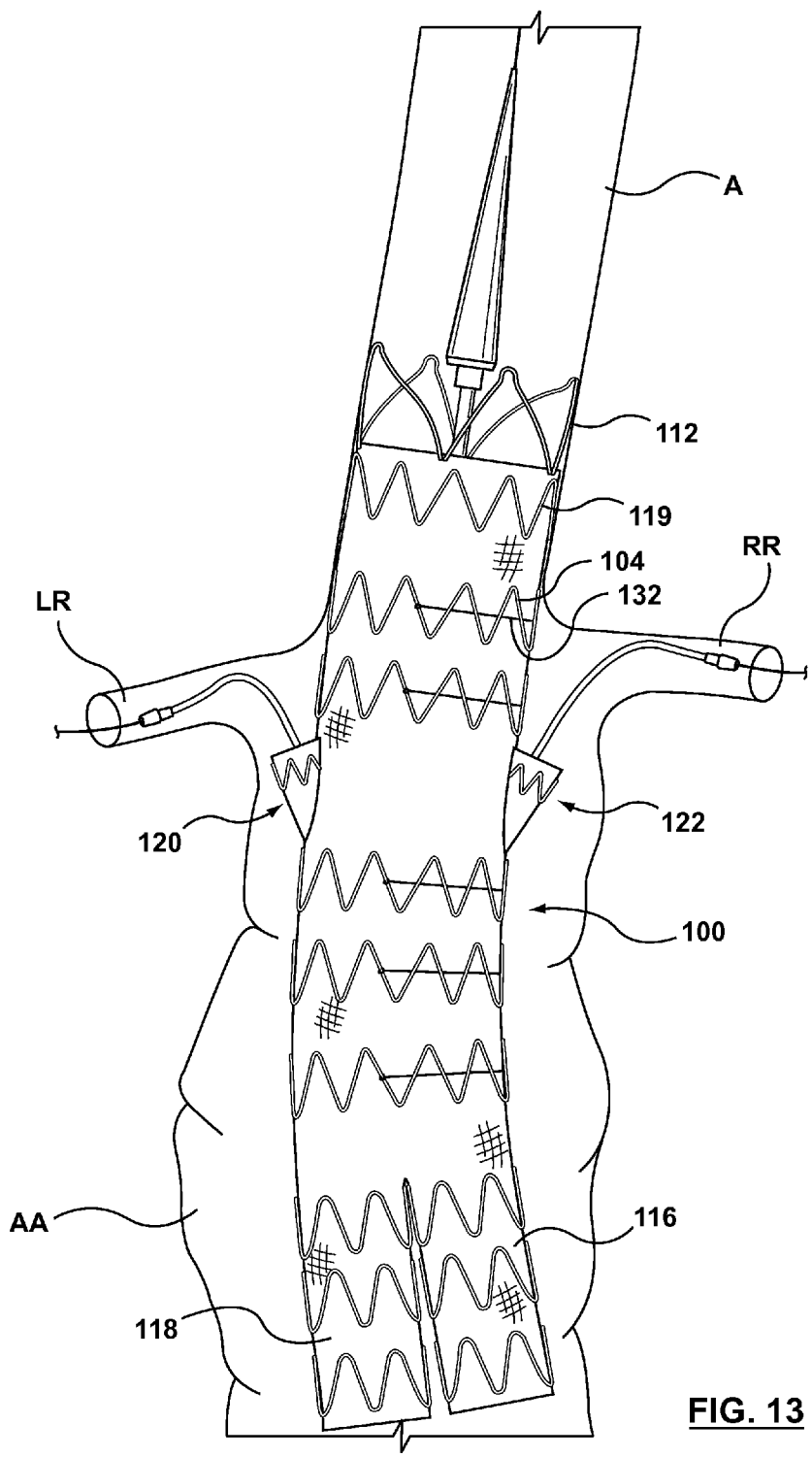

Trigger wire 150 is then retracted proximally (i.e. towards the physician), as shown by the arrow in FIG. 12. As trigger wire 150 moves past stents 104A and 104B, first threads 132A and 132B of circumferentially constraining sutures are released, allowing that portion of stent-graft 100 to expand to the deployed configuration. First threads 132A, 132B remain attached at one end to stents 104A, 104B, respectively, as described above and shown at 148A, and first threads 132A, 130B extend between graft 102 and stents 104A, 104B. Because first threads 132A and 132B are each shorter than the circumference of the deployed stent-graft prosthesis 100, each first thread 132A, 132B extends only partially around the circumference of stent-graft prosthesis 100. Further, since first thread loop 136 (not shown in FIG. 12) of first threads 132A, 132B is not attached to trigger wire 150 or any portion of stent-graft prosthesis 100, first and second threads 132A, 132B do not exert a radial force to constrain stent-graft 100 in a reduced diameter configuration. As trigger wire 150 continues to be retracted proximally, the remaining first threads 132C, 132D, 132E of the respective circumferentially constraining sutures 130 are released, thereby allowing stent-graft 100 to fully deploy, as shown in FIG. 13. In addition, anchor stent 112 may be released from the tip capture mechanism of the delivery system 882, as also shown in FIG. 13. When anchor stent 112 is released from delivery system 882, seal stent 119 fully expands and conformingly engages and seals the edges of scallop 117 with the blood vessel inner wall. Trigger wire 150 for circumferentially constraining sutures 130 may also be used as a capture mechanism (not shown) as described in co-pending U.S. patent application Ser. Nos. 13/457,535 and 13/457,544 to Maggard et al., filed Apr. 27, 2012; and U.S. patent application Ser. Nos. 13/457,537 and 13/457,541 to Argentine et al., filed Apr. 27, 2012, previously incorporated by reference herein in their entirety.

Figure 14:
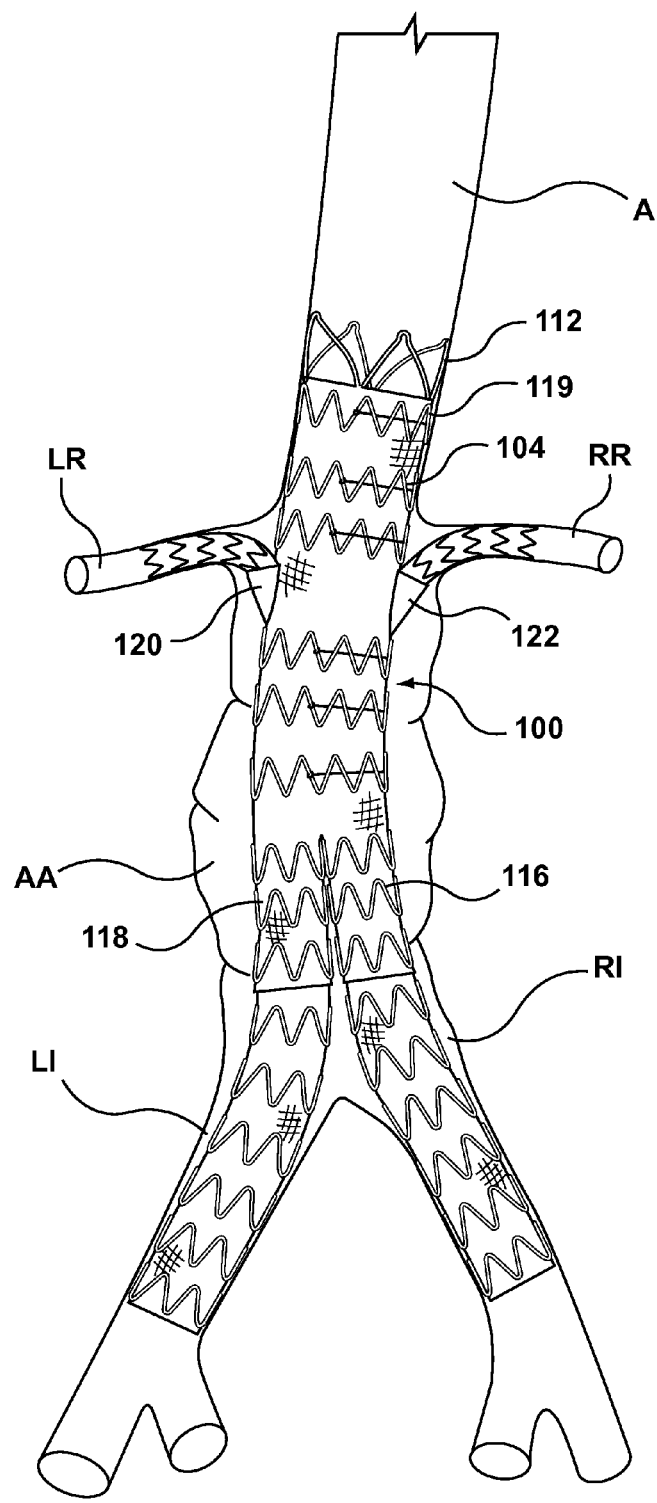

The branch vessel stent-graft prostheses may then be deployed within right renal artery RR and left renal artery LR, respectively, by retracting outer sheaths of the branch vessel stent-graft delivery systems, as known to those skilled in the art and described in co-pending U.S. patent application Ser. Nos. 13/457,535 and 13/457,544 to Maggard et al., filed Apr. 27, 2012 (now published as U.S. Pub. Nos. 2013/0289696 A1 and 2013/0289693 A1, respectively); U.S. patent application Ser. Nos. 13/457,537 and 13/457,541 to Argentine et al., filed Apr. 27, 2012 (now published as U.S. Pub. Nos. 2013/0289691 A1 and 2013/0289692 A1, respectively); and U.S. patent application Ser. Nos. 13/458,209 and 13/458,242 to Coghlan et al., filed Apr. 27, 2012 (now published as U.S. Pub. Nos. 2013/0289701 A1 and 2013/0289702 A1), previously incorporated by reference in their entirety. Further, limb prostheses may be delivered and deployed within legs 116, 118 of main vessel stent-graft prosthesis 100, extending into right iliac artery RI and left iliac artery LI, respectively, as shown in FIG. 14. All the delivery systems are removed, leaving the main vessel stent-graft 100, the branch vessel prostheses, and the limb prostheses, as shown in FIG. 14.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
   a tubular body of a graft material, the tubular body defining a lumen therethrough;
   a stent coupled to the tubular body;
   at least one circumferentially constraining suture configured as a loop; and
   a trigger wire extending longitudinally along the tubular body,
   wherein in a reduced diameter configuration a first end of the loop is attached to the stent, the loop extends only in a first direction from the first end circumferentially around a complete circumference of the tubular body to a second end of the loop disposed opposite the first end, wherein the second end of the loop is coupled to the trigger wire, and
   wherein in a deployed configuration the trigger wire is disengaged from the second end of the loop such that the stent radially expands and the loop extends only partially around the circumference of the tubular body.

2. The endovascular prosthesis of claim 1, wherein the first end of the loop is attached to the stent by tying a first end and a second end of the circumferentially constraining suture to a strut of the stent adjacent to each other.

3. The endovascular prosthesis of claim 1, wherein the first end of the loop is attached to the stent by wrapping a portion of the loop around a strut of the stent and extending a remaining portion of the loop through the portion of the loop wrapped around the strut.

4. The endovascular prosthesis of claim 1, wherein a reduced diameter of the endovascular prosthesis in the reduced diameter configuration at the circumferentially constraining suture is between 40% and 70% of an expanded diameter of the endovascular prosthesis in the deployed configuration at the circumferentially constraining suture.

5. The endovascular prosthesis of claim 1, wherein the stent is coupled to an outside surface of the graft material and the circumferentially constraining suture extends around the outside surface of the graft material between the outside surface and the stent.

6. The endovascular prosthesis of claim 1, wherein the endovascular prosthesis includes five circumferentially constraining sutures.

7. An endovascular prosthesis comprising:
   a tubular body of a graft material, the tubular body defining a lumen therethrough;
   a stent coupled to the tubular body; and
   at least one circumferentially constraining suture, the circumferentially constraining suture comprising,
      a first thread coupled at a first end to the stent and having a first thread loop disposed opposite the first end, the first thread extending only partially around a circumference of the tubular body when the endovascular prosthesis is in a radially expanded configuration, and
      a second thread having a second thread loop interlocked with the first thread loop, the second thread extending from the first thread loop around a remainder of the circumference of the tubular body with the endovascular prosthesis in a radially expanded configuration,
   wherein the circumferentially constraining suture is configured such that pulling the second thread causes the first thread to circumferentially constrain the tubular body such that the tubular body constricts to a reduced diameter configuration.

8. The endovascular prosthesis of claim 7, wherein the first thread is folded to form the first thread loop such that the first end and a second end are disposed adjacent to each other.

9. The endovascular prosthesis of claim 8, wherein the first thread is coupled to the stent by tying the first end and the second end of the first thread to each other to form the first thread loop, wrapping a portion of the first thread loop around a strut of the stent and extending a remaining portion of the first thread loop through the portion of the first thread loop wrapped around the strut.

10. The endovascular prosthesis of claim 7, wherein a distance between the first end of the first thread and the first thread loop where the first thread loop is interlocked with the second thread loop is between 30% and 60% of the circumference of the tubular body in the radially expanded configuration.

11. The endovascular prosthesis of claim 7, wherein the stent is coupled to an outside surface of the graft material and wherein the first thread and the second thread extend around the outside surface of the graft material between the outside surface and the stent.

12. The endovascular prosthesis of claim 7, further comprising a pull tab attached to an end of the second thread opposite the second thread loop.

13. The endovascular prosthesis of claim 7, wherein the endovascular prosthesis includes five circumferentially constraining sutures.

14. The endovascular prosthesis of claim 7, wherein in the reduced diameter configuration, the first thread loop is configured to receive a trigger wire extending longitudinally along the tubular body, and wherein with the trigger wire disposed through the first thread loop, the second thread is configured to be removed from the endovascular prosthesis with the endovascular prosthesis remaining in the reduced diameter configuration.

15. The endovascular prosthesis of claim 1, wherein in the reduced diameter configuration the first end of the loop and the second of the loop are disposed adjacent to each.

16. An endovascular prosthesis comprising:
a tubular body of a graft material, the tubular body defining a lumen therethrough;
a stent coupled to the tubular body;
at least one circumferentially constraining suture including a first end and a second end; and
a trigger wire extending longitudinally along the tubular body,
wherein in a reduced diameter configuration the first end of the circumferentially constraining suture is attached to the stent, the circumferentially constraining suture extends in a first direction circumferentially around a complete circumference of the tubular body from the first end, and the second end of the circumferentially constraining suture is formed into a loop and is coupled to the trigger wire, wherein in the reduced diameter configuration the loop of the circumferentially constraining suture is disposed adjacent to the first end of the circumferentially constraining suture; and
wherein in a deployed configuration the trigger wire is disengaged from the loop such that the stent radially expands and the circumferentially constraining suture extends only partially around the circumference of the tubular body.

17. The endovascular prosthesis of claim 16, wherein a reduced diameter of the endovascular prosthesis in the reduced diameter configuration at the circumferentially constraining suture is between 40% and 70% of an expanded diameter of the endovascular prosthesis in the deployed configuration at the circumferentially constraining suture.

18. The endovascular prosthesis of claim 16, wherein the plurality of stents are coupled to an outside surface of the graft material and the circumferentially constraining suture extends around the outside surface of the graft material between the outside surface and the stent.

* * * * *